(12) United States Patent
Pogue et al.

(10) Patent No.: US 8,886,284 B2
(45) Date of Patent: Nov. 11, 2014

(54) DEVICES AND METHODS FOR COMBINED OPTICAL AND MAGNETIC RESONANCE IMAGING

(75) Inventors: Brian William Pogue, Hanover, NH (US); Colin Morehouse Carpenter, Norwich, VT (US); Scott Christian Davis, Woodsville, NH (US); Keith Douglas Paulsen, Hanover, NH (US); Phaneendra K. Yalavarthy, Hanover, NH (US); Hamid Dehghani, Exeter (GB)

(73) Assignee: The Trustees of Dartmouth College, Hanover, NH (US)

(*) Notice: Subject to any disclaimer, the term of this patent is extended or adjusted under 35 U.S.C. 154(b) by 1441 days.

(21) Appl. No.: 11/831,514

(22) Filed: Jul. 31, 2007

(65) Prior Publication Data

US 2008/0071164 A1    Mar. 20, 2008

Related U.S. Application Data

(60) Provisional application No. 60/834,374, filed on Jul. 31, 2006.

(51) Int. Cl.
| | | |
|---|---|---|
| A61B 5/055 | (2006.01) | |
| A61B 5/00 | (2006.01) | |
| G01R 33/48 | (2006.01) | |
| G01R 33/28 | (2006.01) | |
| G01R 33/341 | (2006.01) | |
| A61B 6/00 | (2006.01) | |
| A61B 6/04 | (2006.01) | |

(52) U.S. Cl.
CPC ............ *A61B 5/4312* (2013.01); *A61B 5/055* (2013.01); *A61B 6/5247* (2013.01); *A61B 6/0414* (2013.01); *G01R 33/4808* (2013.01); *A61B 6/502* (2013.01); *G01R 33/28* (2013.01); *G01R 33/341* (2013.01); *A61B 5/0091* (2013.01)
USPC ............ 600/411; 600/415; 600/421; 600/473

(58) Field of Classification Search
USPC .................................. 600/411, 415, 421, 473
See application file for complete search history.

(56) References Cited

U.S. PATENT DOCUMENTS

| | | | | |
|---|---|---|---|---|
| 4,515,165 | A | * | 5/1985 | Carroll .......................... 600/475 |
| 4,649,275 | A | * | 3/1987 | Nelson et al. .............. 250/358.1 |
| 4,767,928 | A | * | 8/1988 | Nelson et al. .............. 250/341.7 |
| 4,810,875 | A | * | 3/1989 | Wyatt ....................... 250/227.11 |
| 5,730,133 | A | * | 3/1998 | Godik ........................... 600/407 |
| 6,119,033 | A | * | 9/2000 | Spigelman et al. ........... 600/426 |

(Continued)

OTHER PUBLICATIONS

Ntziachristos et al. "Time-correlated single photon counting imager for simultaneous magnetic resonance and near-infrared mammography". Rev. of Scientific Instruments, vol. 69, No. 12, Dec. 1998.*

(Continued)

*Primary Examiner* — Tse Chen
*Assistant Examiner* — Angela M Hoffa
(74) *Attorney, Agent, or Firm* — Lathrop & Gage LLP

(57) ABSTRACT

Optical devices for use with a magnetic resonance imaging breast compression system include light wands and optical adapters that can releasably mate with grids. These devices, and their associated methods, may reduce or eliminate the need for biopsy by allowing for the differentiation of cancerous tumors, non-cancerous tumors, calcifications and cysts.

2 Claims, 11 Drawing Sheets

(56) References Cited

U.S. PATENT DOCUMENTS

| | | | |
|---|---|---|---|
| 7,693,567 B2* | 4/2010 | Tsonton et al. | 600/411 |
| 7,769,426 B2* | 8/2010 | Hibner et al. | 600/411 |
| 2003/0199753 A1* | 10/2003 | Hibner et al. | 600/411 |
| 2003/0199754 A1* | 10/2003 | Hibner et al. | 600/411 |
| 2004/0249268 A1* | 12/2004 | Da Silva | 600/424 |
| 2006/0058703 A1* | 3/2006 | Huenerbein | 600/567 |
| 2007/0173718 A1* | 7/2007 | Richards-Kortum et al. | 600/431 |

OTHER PUBLICATIONS

Brooksby et al. "Spectral priors improve near-infrared diffuse tomography more than spatial priors." Optics Letters, vol. 30, No. 15, Aug. 1, 2005.*

Brooksby et al. "Combining near-infrared tomography and magnetic resonance imaging to study in vivo breast tissue: implementation of a Laplacian-type regularization to incorporate magnetic resonance structure." J. of Biomed. Optics, vol. 10, No. 5, Sep. 2005.*

* cited by examiner

DEVICES AND METHODS FOR COMBINED OPTICAL AND MAGNETIC RESONANCE IMAGING

RELATED APPLICATIONS

This application claims the benefit of priority to commonly-owned and U.S. Provisional Patent Application No. 60/834,374, filed 31 Jul. 2006, which is incorporated herein by reference.

U.S. GOVERNMENT RIGHTS

This invention was made with Government support under grant nos. RO1CA69544, RO1CA109558, PO1CA80139 and U54CA105480, awarded by the National Institutes of Health, and grant no. DAMD17-03-1-0405, awarded by the Department of Defense. The Government has certain rights in this invention.

BACKGROUND

X-ray mammography is generally regarded as the single most important tool in the early detection of breast cancer. Mammography detects 85-90% of breast cancers, and the American Cancer Society recommends that women age forty and older undergo yearly screening. The main drawback of mammography is that it has a low positive predictive value which frequently necessitates additional testing, such as more intensive mammography, magnetic resonance (MR) imaging, ultrasound and/or biopsy.

MR imaging produces higher resolution images of deeper and/or denser tissue than mammography, without the use of ionizing radiation. However, MR instruments are expensive to own and operate, and the resulting images suffer from the same low positive predictive value as mammograms. Masses detected by MR imaging require further evaluation, such as by ultrasound, which can distinguish between solid tumors and cysts, and/or biopsy, which is an invasive and unpleasant procedure.

As an alternative to biopsy, optical imaging of tissue is an emerging modality for detection, diagnosis and monitoring of breast cancer. Diffuse optical tomography uses electromagnetic energy, ranging from visible light to near infrared (NIR), to probe objects beneath the skin surface, such as tissue, fluid and tumors. Information about tissue composition and morphology is gained by measuring and modeling light absorption, scattering and emission. This information can be used to create two-dimensional cross-sectional slices and/or three-dimensional images, and also to distinguish between cancerous tumors, non-cancerous tumors, calcifications and cysts. For example, when light is absorbed by a compound (chromophore) within the tissue, the chromophore, such as hemoglobin, lipid or water, can be identified and quantified. Tumors frequently have increased blood flow, so that a high concentration of hemoglobin may be indicative of a tumor. Further, intense scattering of light may be attributed to a solid or semi-solid mass, such as a tumor.

Qualitative, moderate-resolution optical images have been used to diagnose tumors based on their metabolic and functional status, but improvements in quantitative accuracy and resolution may be obtained when anatomical information from other modalities, such as MR imaging or ultrasound, is used in the image reconstruction procedure. Hybrid instrumentation and methodologies for incorporating anatomical information as spatial priors into tissue reconstruction algorithms are currently being developed, and can significantly improve the accuracy of the recovered information by identifying borders between different tissue types, as observed by MR.

One hybrid system for combined optical and MR imaging is described in V. Ntziachristos, X. H. Ma, and B. Chance, "Time-correlated single photon counting imager for simultaneous magnetic resonance and near-infrared mammography", Rev. Sci. Instrum., 69(12), 4221-4233, December 1998. This system utilizes a pair of soft compression plates that contain MR radio frequency coils, as well as optical fibers. The medial compression plate contains optical source fibers and the lateral compression plate contains optical detector fibers, so that light transmission may be detected.

Such specialized systems are infrequently adopted as replacements for current industry standards because they are viewed as time consuming and troublesome. For example, the orientation and field gradient of the above-described integrated radio frequency coils must be recalibrated for each patient, and the system does not allow for biopsy access. A physician must therefore choose, before placing the patient into the bore of the MR instrument, whether a mass (if observed) will be optically imaged, using the specialized compression system, or biopsied, using a traditional compression system. If the physician chooses optical imaging and later, based on the optical imaging results, decides to biopsy the mass, the patient must be removed from the MR instrument, outfitted with a different compression system, placed back in the instrument and a new series of scans must be taken to relocate the mass. This extra procedure is an expensive and arduous task ties up valuable medical resources.

SUMMARY

In one embodiment, an optical adapter for combined optical imaging and magnetic resonance imaging of breast tissue includes a housing having an optical window, wherein a portion of the housing containing the optical window releasably mates with a grid hole of a breast tissue compression system.

In one embodiment, a method of optically imaging breast tissue includes coupling an optical adapter with a grid of a magnetic resonance imaging breast tissue compression system and obtaining optical data.

In one embodiment, a method uses spatial priors to increase the resolution and accuracy of a near infrared image reconstruction of tissue. The image reconstruction, which involves the use of a regularization reconstruction algorithm, is improved by incorporating a filter matrix into the regularization reconstruction algorithm, wherein the filter matrix is generated by assigning each node in a finite element method mesh to a tissue type.

In one embodiment, a software product includes instructions, stored on computer-readable media, wherein the instructions, when executed by a computer, perform steps for creating a tomographic image of tissue. The instructions include: instructions for obtaining magnetic resonance (MR) data associated with the tissue; instructions for generating a finite element method mesh from the MR data; instructions for assigning each node in the finite element method mesh to a tissue type; instructions for using the tissue type to generate a filter matrix for use in a regularization reconstruction algorithm; instructions for obtaining near infrared data associated with the tissue; instructions for using the magnetic resonance data that has been generated by the regularization reconstruction algorithm to spatially constrain the near infrared data algorithm; and instructions for creating a tomographic image of the tissue.

DETAILED DESCRIPTION

Optical devices for use with a MR imaging breast compression system are disclosed herein. Use of these devices and related methods may, for example, allow for non-invasive differentiation between cancerous tumors, non-cancerous tumors, calcifications, cysts, fatty tissue and fibroglandular tissue.

Reference will now be made to the attached drawings, where like numbers represent similar elements in multiple figures. Numbering without parentheses is used to denote a genus (e.g., optical adapter 400), whereas numbering with parentheses denotes a species within a genus (e.g., optical adapter 400(2)). Multiple elements within a figure may not be labeled for the sake of clarity.

Figure 1:
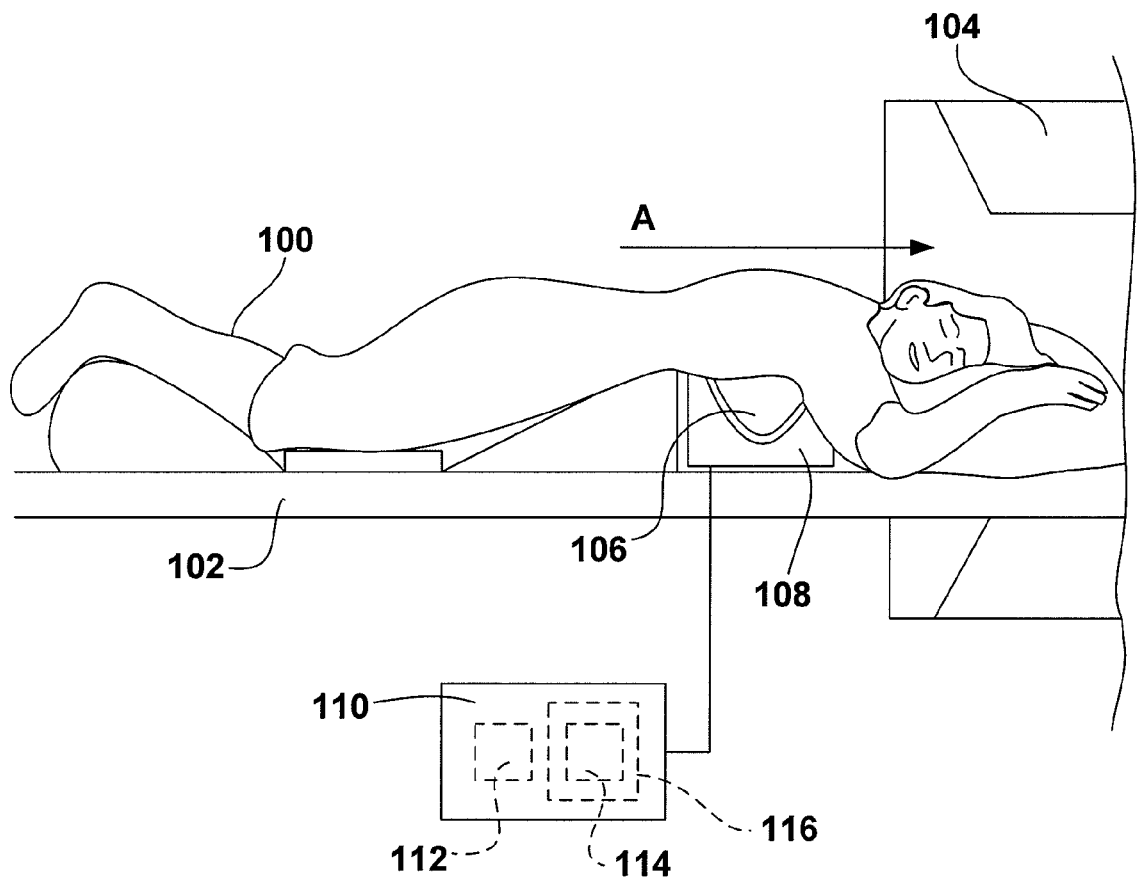
FIG. 1 shows a side plan view of a patient positioned for magnetic resonance imaging of breast tissue.

FIG. 1 shows a side plan view of a patient 100 positioned for MR imaging of breast tissue. Patient 100 lies prone on an MR imaging table 102, which slides, in the direction of arrow A, into the bore of an MR instrument 104. The patient's breast 106 is positioned in a breast coil 108. Breast coil 108 is used to apply a radio frequency pulse that excites hydrogen atoms in the body (e.g., water) to a high-energy state. When the radio frequency pulse is turned off, the hydrogen atoms release energy as they return to a lower energy state. Breast coil 108 detects the released energy, and transmits data to a computer 110. A microprocessor 112 executing software 114, within a memory 116 of computer 110, may manipulate the data to create an image of breast 106. Memory 116 may, for example, represent one or more of random access memory (RAM), erasable programmable read-only memory (EPROM), programmable read only memory (PROM) and non-volatile random access memory (NVRAM) (e.g., flash memory), or other types of non-volatile storage.

Figure 2:
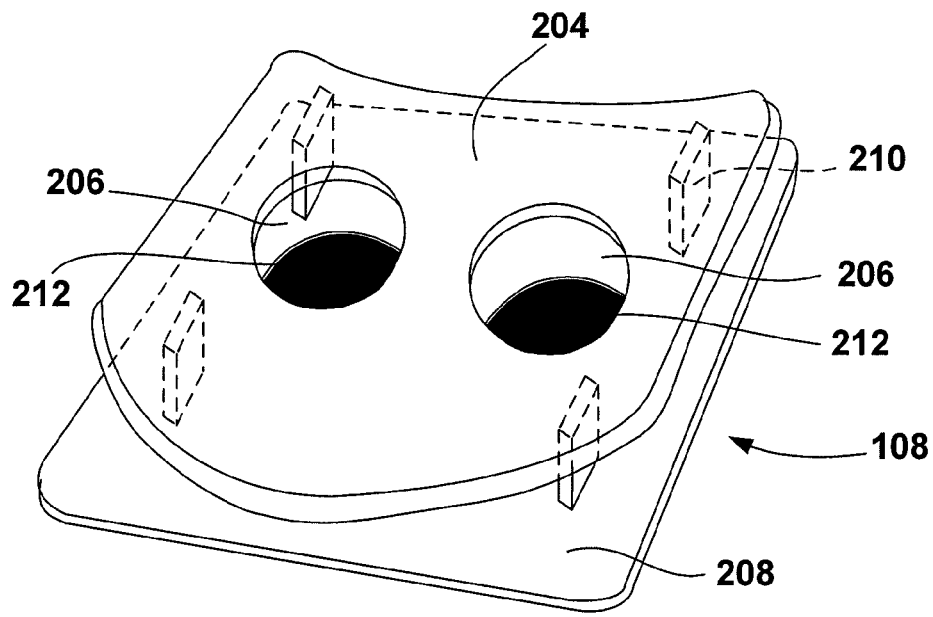
FIG. 2 illustrates a breast coil and compression system for use during magnetic resonance imaging.
Figure 2:
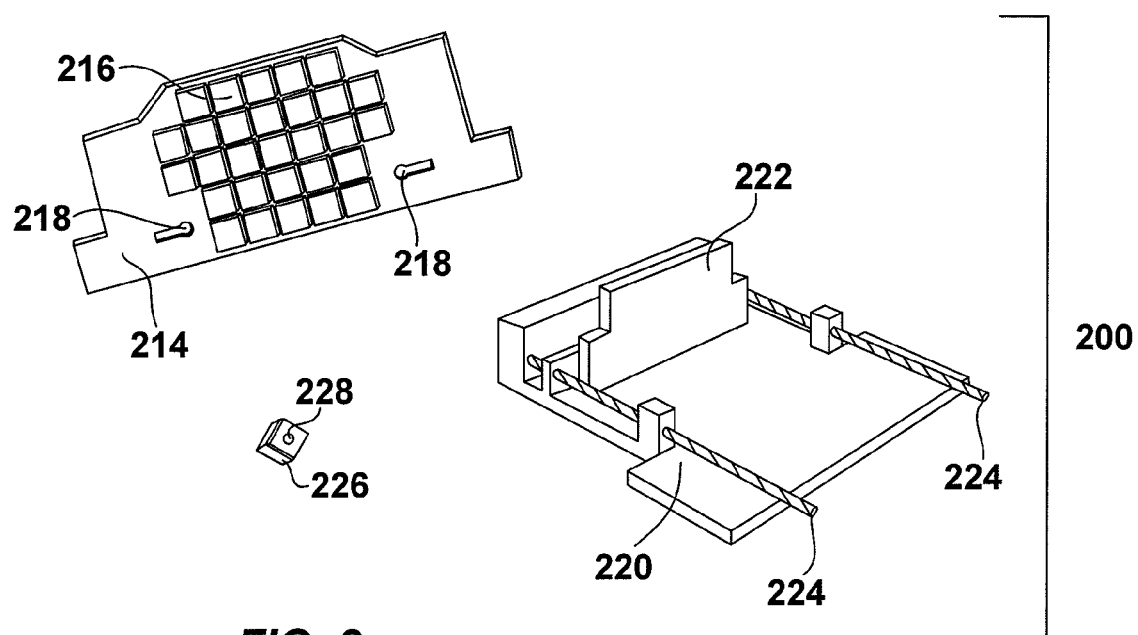
Figure 3:
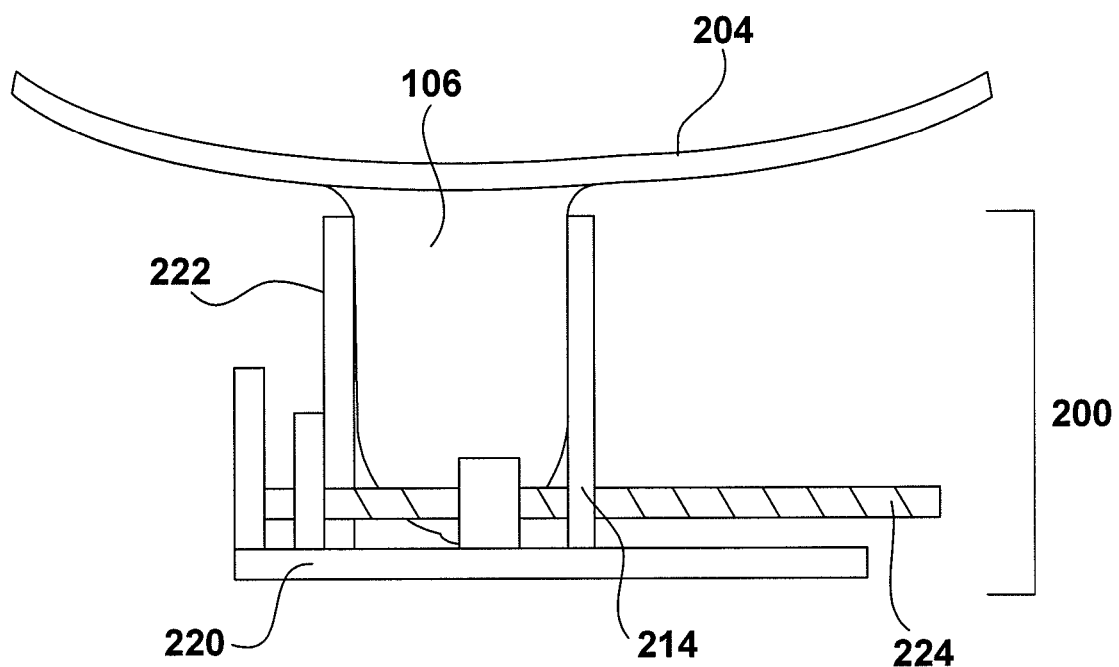
FIG. 3 illustrates an inferior sagittal view of a right breast immobilized in the compression system of FIG. 2.

FIG. 2 illustrates a breast coil 108 and compression system 200 for use during magnetic resonance imaging. Breast coil 108 includes a body cradle 204 that supports the torso of patient 100. Body cradle 204 has one or two openings 206 that receive the patient's breast(s) 106. Body cradle 204 is separated from a base 208 by pedestals 210. Base 208 may include one or more openings 212 in vertical alignment with openings 206. Compression system 200 is used to immobilize breast tissue during imaging and biopsying. In operation, compression system 200 is disposed between body cradle 204 and base 208 of breast coil 108. Compression system 200 includes a grid 214, a compression plate 220 and a biopsy needle guide 226. Compression plate 220 includes a wall 222 that abuts the medial edge of breast 106. A pair of threaded guides 224 allows compression plate 220 to be mated with grid 214 via guide holes 218. Grid 214 abuts the lateral edge of breast 106. Grid 214 may be held in place by fasteners (not shown) that screw onto threaded guides 224. Grid 214 includes a plurality of grid holes 216 that provide access to breast 106 and directional guidance during biopsying. Biopsy needle guide 226 may be inserted into one of grid holes 216 and a biopsy needle (not shown) may be inserted through opening 228. FIG. 3 shows an inferior sagittal view of a right breast 106 immobilized in compression system 200 of FIG. 2.

Figure 4:
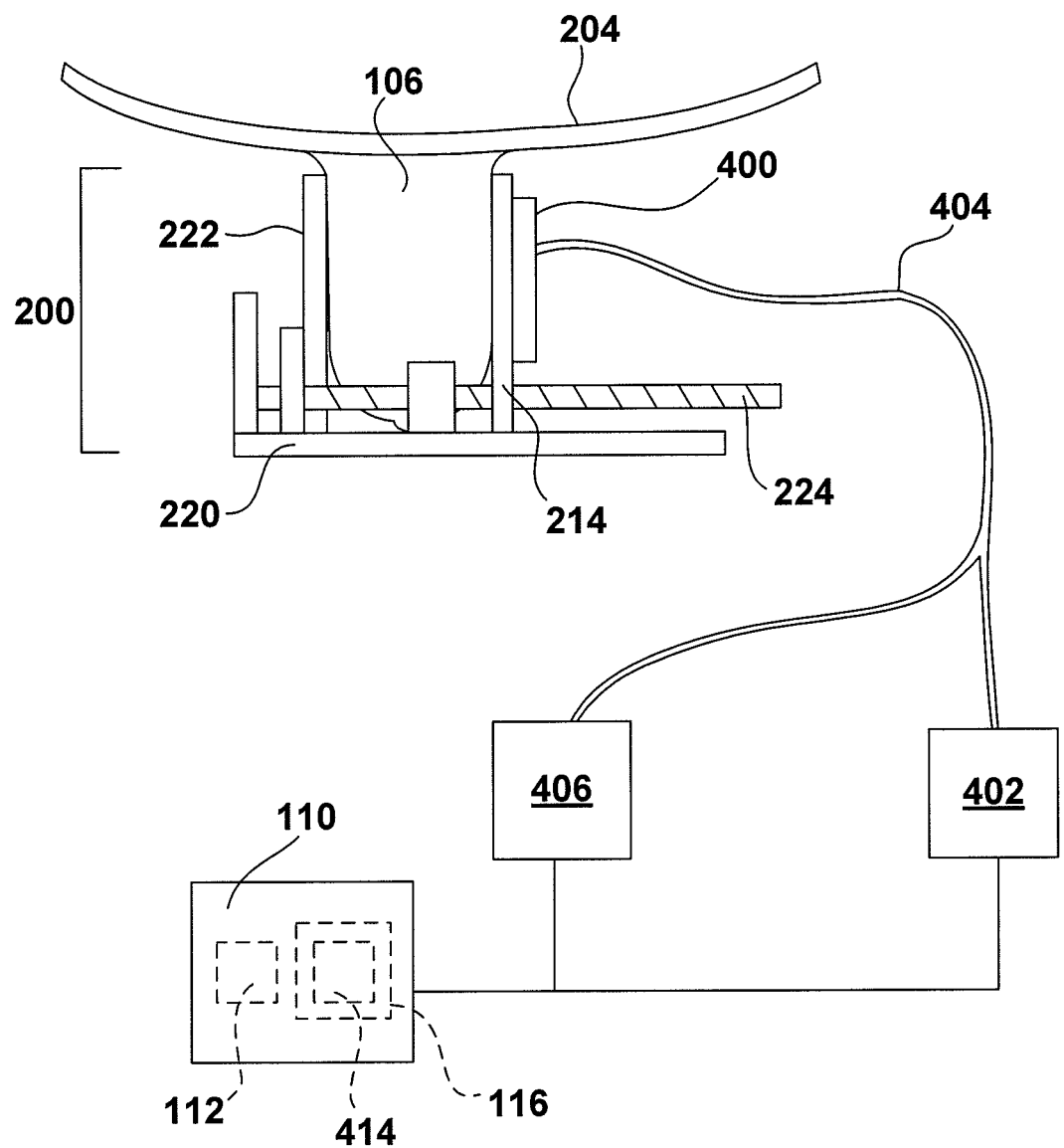
FIG. 4 illustrates the system of FIG. 3 further including an optical adapter, according to one embodiment.

FIG. 4 illustrates the system of FIG. 3 further including an optical adapter 400. Optical adapter 400 is a modular device that can mate with grid 214. Optical adapter 400 delivers electromagnetic energy, $\lambda$, produced by an excitation unit 402 and transmitted through fiber optics 404, to breast tissue 106. Excitation unit 402 may have one or more of a white light, laser or light emitting diode source. Electromagnetic energy that is reflected and/or emitted by breast tissue 106 is transmitted through optical adapter 400 to fiber optics 404. The reflected and/or emitted light is transmitted to a detector 406. Depending upon the wavelength range of interest, detector 406 may, for example, be a photodiode, spectrometer, CCD and/or a microbolometer. Detector 406 transmits raw data to computer 110, where the data may be stored to memory 116 and manipulated by microprocessor 112 executing software 414. Tomographic images may be generated from the manipulated data as concentration maps displaying a chromophore concentration, a fluorophore concentration, scatter amplitude, and/or scatter power as a spatial function.

In one embodiment, wall 222 may be replaced by a grid 214 and, optionally, an optical adapter 400. Replacement of wall 222 may, for example, be useful when optical imaging and/or biopsy are to be performed on a suspected tumor that is proximal to the medial edge of breast 106, or when electromagnetic energy produced at the lateral edge of breast 106 cannot penetrate the entire tissue volume. Electromagnetic energy in the near infrared (NIR) region is known to penetrate breast tissue to a depth of about 15 cm; however, some women have breast tissue that exceeds this range and others, especially young women, have dense breast tissue which may limit light penetration to less than 15 cm. In another embodiment, use of multiple grids and optical adapters may provide more comprehensive and/or more accurate results than data obtained from a single optical adapter 400. For example, a configuration containing two grids, each coupled to an optical adapter, may allow for measurement of transmitted light—in addition to reflected and emitted light.

Figure 5:
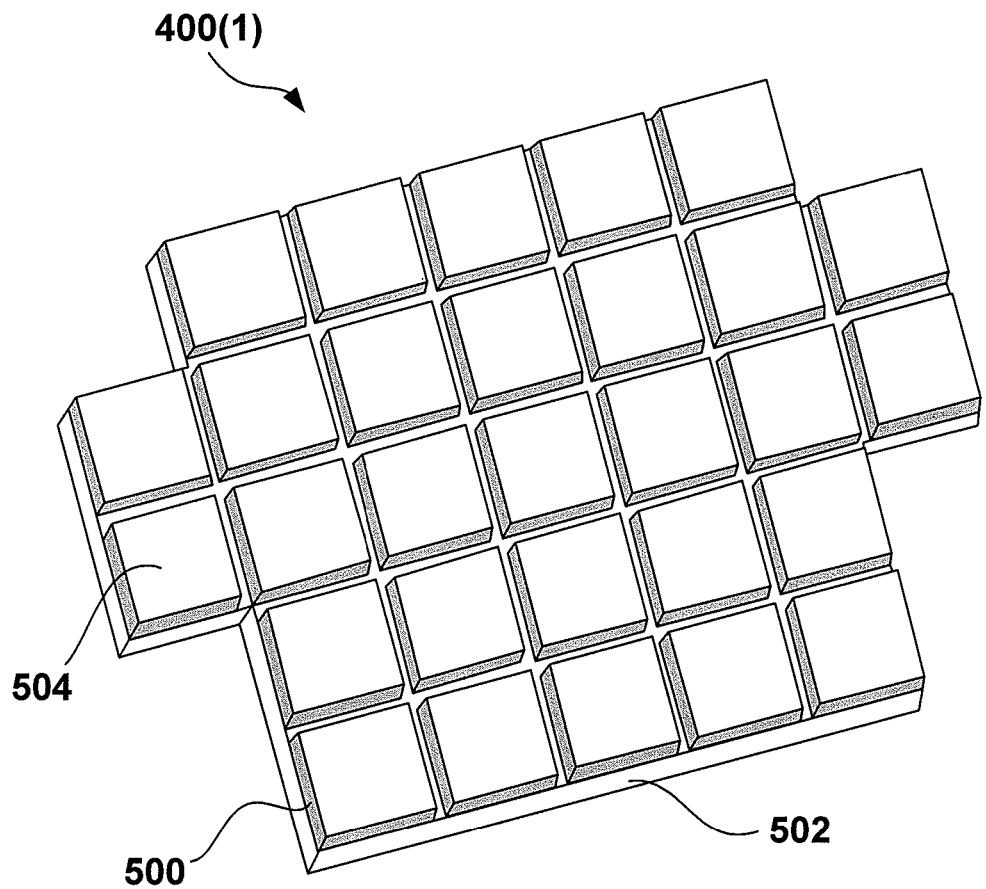
FIG. 5 illustrates a perspective view of an optical adapter, according to one embodiment.
Figure 6:
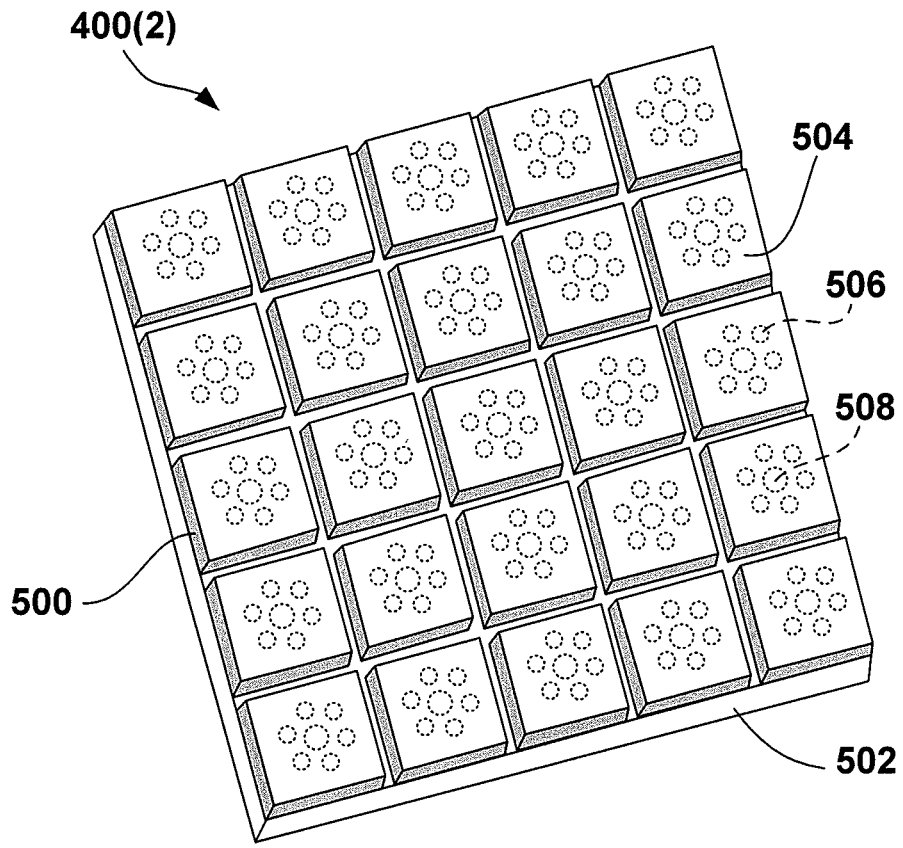
FIG. 6 illustrates a perspective view of another optical adapter, according to one embodiment.
Figure 7:
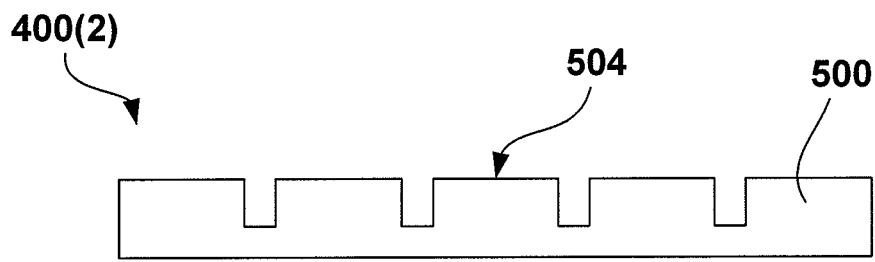
FIG. 7 illustrates a side plan view of an optical adapter.
Figure 8:
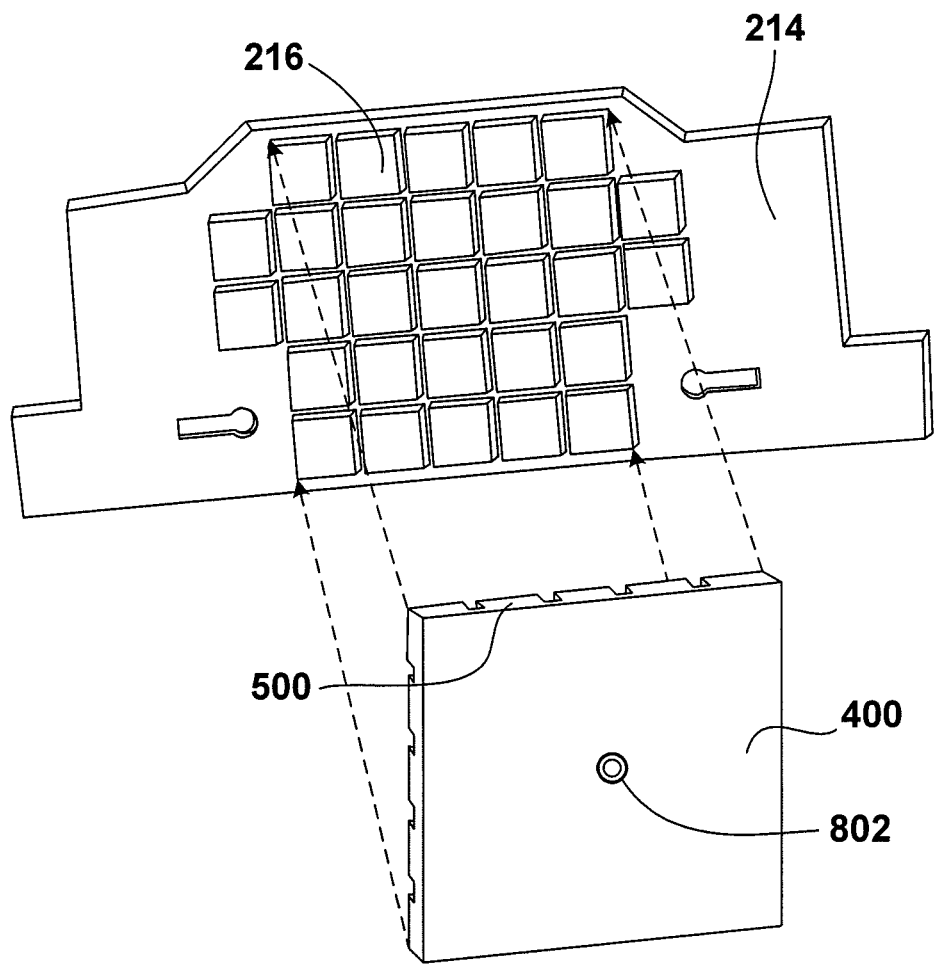
FIG. 8 shows the connectivity between a grid and an optical adapter.

FIG. 5 illustrates a perspective view of an optical adapter 400(1). Optical adapter 400(1) includes a housing 502 having protrusions 500 that fit into grid holes 216. Protrusions 500 include optical windows 504 that are transparent to a specified range of electromagnetic energy, e.g., visible and/or near infrared energy ($\lambda$=650-900 nm). Suitable transparent materials for the visible and near infrared spectral range include quartz, polystyrene, polycarbonate and polypropylene. FIG. 6 illustrates a perspective view of another optical adapter 400(2), which is formed as a 5×5 matrix of protrusions 500. Each protrusion 500 includes one or more source fibers 506 and one or more detector fibers 508. In the example shown, six source fibers 506 surround one detector fiber 508. It will be appreciated, however, that the number and configuration of source and detector fibers may vary. A side plan view of optical adapter 400(2) is shown in FIG. 7. The connectivity between grid 214 and optical adapter 400 is shown in FIG. 8. A fiber optic connection port 802 disposed on the posterior portion of optical adapter 400 is also visible in FIG. 8.

Clamps, brackets, adhesives or other means of securing optical adapter 400 to grid 214 may be integrated with or utilized in conjunction with optical adapter 400 and/or grid 214.

Figure 9:
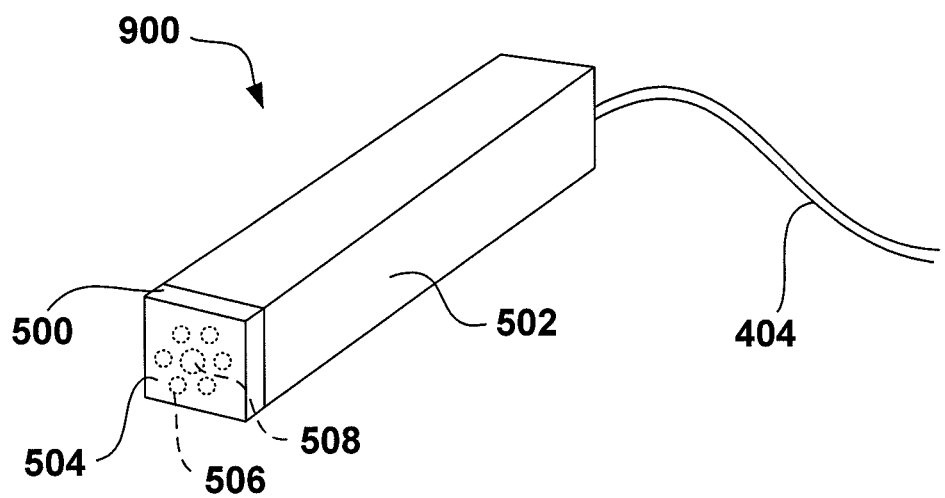
FIG. 9 illustrates an optical adapter in the form of a light wand, according to one embodiment.

FIG. 9 illustrates an optical adapter in the form of a light wand 900 having a housing 502 and a single protrusion 500. For ease of fabrication, it will be appreciated that optical window 504 may be fixedly attached to protrusion 500, which may subsequently be connected to housing 502. In an alternate embodiment, protrusion 500 may be excluded and optical window 504 may be joined directly with housing 502. Light wand 900 may be used to investigate a suspicious area, which has been detected by MR imaging. Light wand 900 may be oriented in grid 214 according to protocols currently used for orienting biopsy needle guide 226. In an alternate embodiment, light wand 900 is sized and shaped to fit in opening 228 of biopsy needle guide 226.

The optical devices and associated components described herein may be located in or near the magnetic field of an MR instrument. They should therefore be fabricated from non-magnetic materials such as plastic, glass, rubber, carbon fiber, non-magnetic metals (e.g., Ti, Zr, Zn, Sn, Cu, Ag, Au) and combinations thereof. Any magnetic materials that are necessary within the optical devices and associated components are shielded.

Imaging agents may be used to improve the specificity and sensitivity of measurements. For example, to improve the quality of MR images, magnetic particles, such as gadolinium, may be injected into a patient's circulatory system directly upstream from a tissue to be imaged. In diffuse optical tomography, intravenous administration of iodocyanine green is common. For both types of imaging, molecular specific contrast agents are currently being developed. Molecular specific contrast agents selectively target tumors expressing certain proteins. They may, therefore, be used to identify a tumor and gain knowledge of its immunohistochemistry, which may help physicians prescribe targeted pharmaceuticals.

Image accuracy and quality may also be improved by the use of prior information in an image reconstruction methodology. An example illustrating the use of prior information in image reconstruction is provided below. This example is for purposes of illustration only and nothing therein should be construed as limiting the scope of what is described and claimed.

Example 1

Use of a Laplacin-Type Regularization to Incorporate Magnetic Resonance Structure into NIR Images Early work on incorporating prior knowledge of tissue structure from MR data into NIR reconstructions imposed constraints on neighboring pixels such that within homogeneous regions the pixels had similar intensity levels, and, in regions that exhibited distinctly different tissue characteristics, smoothing across the shared boundary was limited. It was further assumed that optical contrast correlated to MR contrast. While generally effective in simulation studies, and for reconstructing simple phantom geometries containing a single discrete heterogeneity (i.e., inclusion), these methods proved vulnerable to over-biasing the inverse solutions toward the assumed distributions. Sensitivity to noise in the data and error in the region designation caused the algorithms to be unreliable when imaging complex and layered phantoms.

The present method guides the iterative evolution of reconstruction, but does not impose a rigid constraint of interregion homogeneity. Portions of the present method are described in B. Brooksby, S. Jiang, H. Dehghani, B. W. Pogue, K. D. Paulsen, J. Weaver, C. Kogel, S. P. Poplack "Combining near-infrared tomography and magnetic resonance imaging to study in vivo breast tissue: implementation of a Laplacian-type regularization to incorporate magnetic resonance structure", J. Biomed. Optics 10(5), 051504, September/October 2005 and B. Brooksby, S. Srinivasan, S. Jiang, H. Dehghani, B. W. Pogue, K. D. Paulsen, J. Weaver, C. Kogel, S. P. Poplack "Spectral priors improve near-infrared diffuse tomography more than spatial priors" Optics Letters, 30(15), 1968-1970, Aug. 1, 2005, both of which are incorporated herein by reference.

Figure 10:
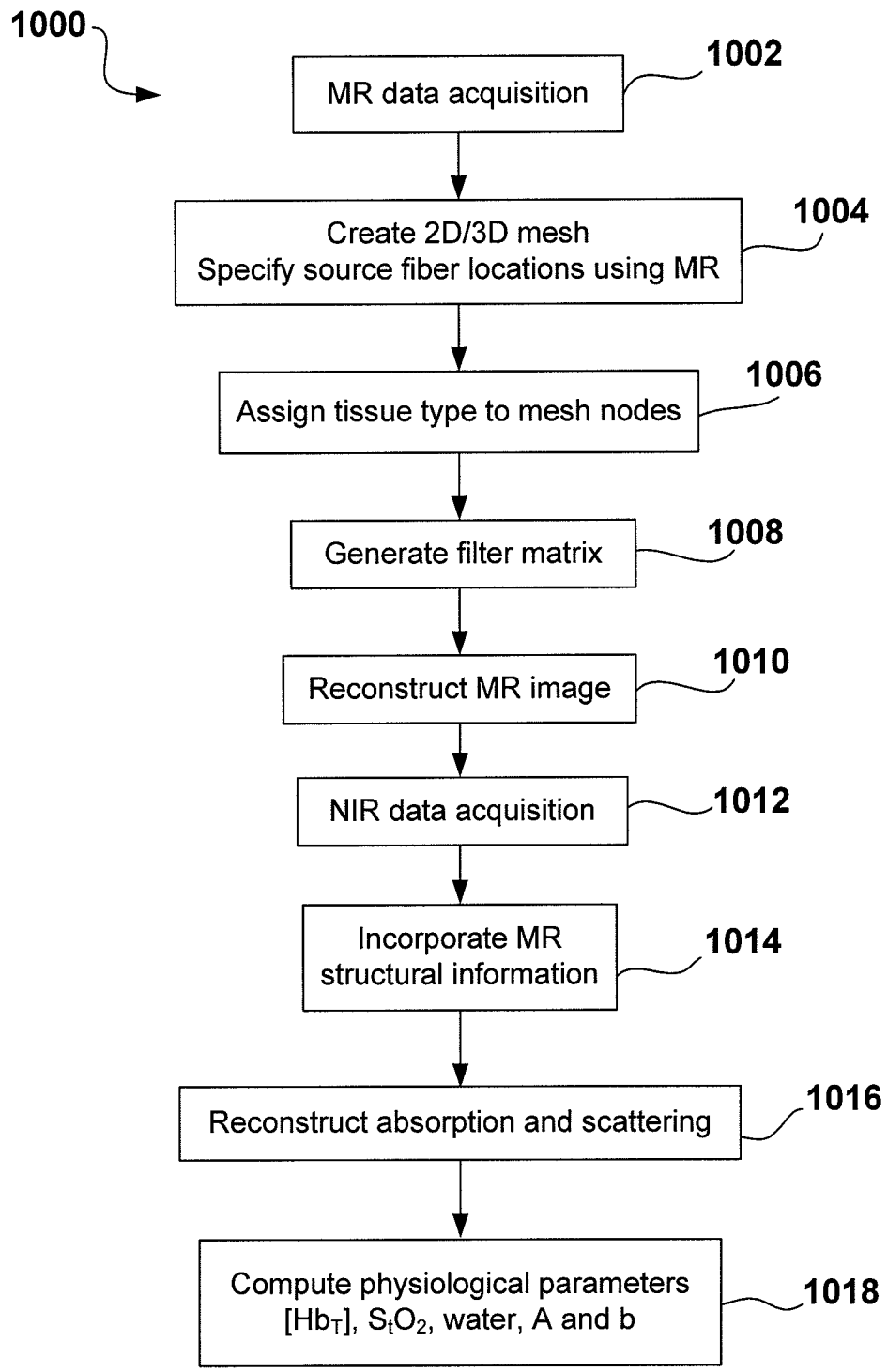
FIG. 10 illustrates one process for constraining a near infrared image with magnetic resonance data, according to one embodiment.

FIG. 10 illustrates one process 1000 for constraining a near infrared image with MR data. Process 1000 begins with the acquisition of MR data in step 1002. In step 1004, a two-dimensional or three-dimensional finite-element method mesh may be generated from the MR data, and NIR source fiber locations may be located, e.g., by the presence of fiduciaries, and correlated with the MR mesh. In step 1006, tissue types (e.g., adipose or fibroglandular) may be assigned to each node in the mesh, and in step 1008, these tissue types may be used to generate a filter matrix for incorporation into a regularization reconstruction algorithm that is used in step 1010 to reconstruct the MR image. In step 1012, NIR data may be acquired, although it will be appreciated by those skilled in the art that MR and NIR data may be acquired simultaneously in some embodiments of process 1000. In step 1014, the MR structural information may be used to constrain the NIR reconstruction. In step 1016, absorption and scattering may be reconstructed at one or more wavelengths. In step 1018, physiological parameters, such as $[Hb_T]$, $S_tO_2$, $H_2O$, A and b, may be computed.

Figure 11:
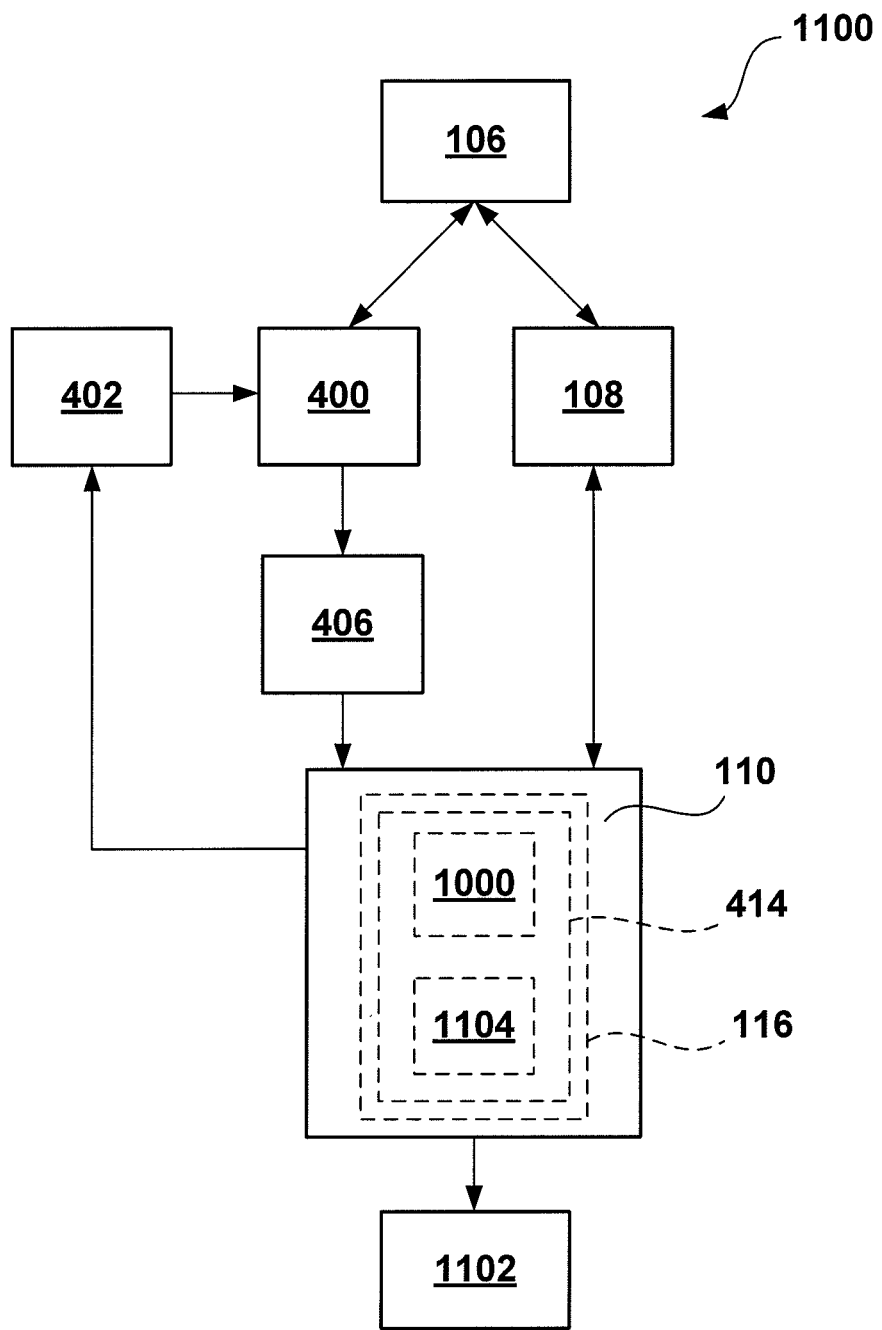
FIG. 11 illustrates a block diagram of a system for implementing the process shown in FIG. 10.

FIG. 11 shows a block diagram 1100 of a system for implementing the process shown in FIG. 10. System 1100 includes tissue 106, optical adapter 400, excitation unit 402, detector 406, breast coil 108, computer 110 and a display 1102. A tissue model, or phantom, may be used in place of tissue 106 during development and calibration. Excitation unit 402 and breast coil 108 are controlled by computer 110 executing software 414 that performs the steps of process 1000. NIR and MR signals are measured by detector 406 and breast coil 108, respectively. The measured data are acquired (FIG. 10, steps 1002, 1012) by computer 110, and may, for example, be stored in memory 116. Process 1000 is then used to manipulate the data and the resulting absorption, scattering and physiological parameters (FIG. 10, steps 1016, 1018) are used to generate a tomographic image using algorithms known in the art, which are executed according to the steps of process 1104. The tomographic image may be viewed on display 1102.

Image Formation

It is well established that in the interaction of NIR light with tissue, scattering dominates over absorption. Under these conditions, light transport can be effectively modeled using the diffusion equation over moderately large distances. A frequency-domain diffusion model is used to simulate measured signals for any specified distribution of absorption and reduced scattering coefficients, $\mu_a$ and $\mu'_s$, within an imaged volume. This is given by:

$$-\nabla \cdot D(r)\nabla\Phi(r,\omega) + \left[\mu_a(r) + \frac{i\omega}{c}\right]\Phi(r,\omega) = S(r,\omega), \quad (1)$$

where $S(r,\omega)$ is an isotropic light source at position r, $\Phi(r,\omega)$ is the photon density at r, c is the speed of light in tissue, $\omega$ is the frequency of light modulation, and $D=1/[3(\mu_a+\mu'_s)]$ is the diffusion coefficient. The reduced scattering coefficient is given by $\mu'_s=\mu_s(1-g)$, where g is the mean cosine of the single scatter function (the anisotropy factor), and $\mu_s$ is the scattering coefficient. A type III boundary condition is applied as:

$$\Phi + \frac{D}{\alpha}\hat{n}\cdot\nabla\Phi = 0, \quad (2)$$

where $\alpha$ is a term that incorporates reflection as a result of refractive index mismatch at the boundary, and $\hat{n}$ is the outward-pointing normal to the boundary.

Eq. (1) can be viewed as a nonlinear function of the optical properties. Its solution is represented as a complex-valued vector, $y=F(\mu_a, D)$ (F representing the model), having real and imaginary components that are transformed to logarithm of the amplitude and phase in the measurements. The phase shift of the signal provides data that is dominated by the optical path length through tissue, while the amplitude of the transmitted light provides information about the overall attenuation of the signal. These measurements constitute the dataset necessary for successful estimation of both absorption and reduced scattering coefficients.

Data acquired by the detection system is typically processed with a finite element method (FEM)-based reconstruction algorithm to generate tomographic images of $\mu_a$ and $\mu'_s$. In the image reconstruction, a Newton-minimization approach is used to seek a solution to:

$$(\hat{\mu}_a,\hat{D})=\min_{\mu_a,D}\{\|y^*-F(\mu_a,D)\|+\lambda\|(\hat{\mu}_a,\hat{D})-(\mu_{a,0},D_0)\|\}, \quad (3)$$

where $\|\cdot\|$ represents the square root of the sum of squared elements, and $\lambda$ is a weighting factor of the difference between the current values of the optical properties and their initial estimates and data-model misfit ($y^*-F(\mu_a, D)$, where $y^*$ is the experimental data). The magnitude of this objective function is sometimes referred to as the projection error and provides a value for determining the convergence of the iterative solution. Its minimum is evaluated by setting first derivatives with respect to $\mu_a$ and D equal to zero. This leads to a set of equations that can be solved iteratively, using the following matrix equation derived from Eq. (3):

$$\delta\mu=(J^TJ+\lambda I)^{-1}[J^T[y^*-F(\mu_a,D)]-\lambda(\mu-\mu_0)]. \quad (4)$$

where $\mu$ denotes the optical parameters being reconstructed and $\mu_0$ is the original estimate. At each iteration, the new set of $\mu_a$ and D values is updated by $\mu_a^{i+1}=\mu_a^i+\delta\mu_a^i$, and $D^{i+1}=D^i+\delta D^i$, where i is the index for the iteration number, J is the Jacobian matrix for the diffusion equation solution, and $J^TJ$ is ill-conditioned and therefore regularized through the addition of $\lambda I$, where I is an identity matrix. Regularization is implemented in a Levenberg-Marquardt algorithm where $\lambda$ starts at a high value (typically ten times the maximum value of the diagonal of $J^TJ$) and can then be systematically reduced at each iteration. In Eq. (4), $\mu_0$ is the initial estimate of optical properties input into the iterative estimation process, and is a form of prior information. Here, the initial estimate is determined through a data calibration procedure which assumes a homogeneous property distribution.

Inclusion of Priors

A priori information can be incorporated directly through the objective function by formulating the minimization of a two term functional:

$$(\hat{\mu}_a,\hat{D})=\min_{\mu_a,D}\{\|y^*-F(\mu_a,D)\|+\alpha\|[L(\hat{\mu}_a,\hat{D})-(\mu_{a,0},D_0)]\|\}. \quad (5)$$

The constant $\alpha$ balances the effect of the prior with the data-model mismatch. The filter matrix L is generated using MR-derived priors and effectively relaxes the smoothness constraints at the interface between different tissues, in directions normal to their common boundary. The effect on image quality is similar to that achieved through total variation minimization schemes. This procedure, however, is more robust and can easily encode internal boundary information from MR images. Each node in the FEM mesh is labeled according to the region, or tissue type, with which it is associated (in the MR image, e.g., adipose or fibroglandular). For the i'th node of n in region N, $L_{i,i}=1$. When nodes i and j are in the same region, $L_{i,j}=-1/n$, otherwise $L_{i,j}=0$. The solution to Eq. (5) is accomplished with a Newton-minimization approach, that produces the update equation:

$$\delta\mu=(J^TJ+\alpha L^TL)^{-1}[J^T[y^*-F(\mu_a,D)]-\alpha L^TL[(\hat{\mu}_a,\hat{D})-(\mu_{a,0},D_0)]], \quad (6)$$

which can also be iteratively solved. Note $L^TL$ approximates a second-order Laplacian smoothing operator within each region separately. This construction of L has proved flexible and effective, but other forms can easily be implemented and evaluated.

Simulation studies were performed to characterize the effect of L and $\alpha$ on the quality and quantitative accuracy of reconstructed images, and to establish a value of $\alpha$ that can be used routinely. Data was generated from numerical phantoms with a variety of heterogeneity patterns—ranging from a simple circular anomaly in a homogeneous background to irregular distributions of regions with two or three different properties. Noise (1% to 2%) was added to simulated data to better replicate experimental conditions. Error was also added to the a priori region designation, to account for the small loss of resolution when spatial information is transferred from MR images to FEM meshes. Images were reconstructed from this data using a range of $\alpha$ from 1 to 100. A high $\alpha$ value increases the impact of the spatial prior, leading to images with sharper internal boundaries, but could negatively bias solutions if this prior is not correct. By accounting for the different sources of error that can be present when data is acquired, simulation results indicate that setting $\alpha$ to ten times the maximum value of the diagonal of $J^TJ$ optimizes image quality and accuracy regardless of the level of geometric complexity present in the area under investigation.

Spectral Decomposition

The absorption coefficient at any wavelength is assumed to be a linear combination of the absorption due to all relevant chromophores in the sample:

$$\mu_a(\lambda) = \sum_{i=1}^{N} \varepsilon(i,\lambda)C_i, \quad (7)$$

where $\lambda$ is the molar absorption spectra, and C is the concentration of each chromophore. The concentrations of three chromophores—oxyhemoglobin ($HbO_2$), deoxyhemoglobin (Hb) and water (H$_2$O)—are estimated. Hence, given $\mu_a$ at the k'th pixel for multiple wavelengths, a linear inversion of Eq. (7) determines the array of C values:

$$C_k = E^{-1} \mu_{a,k}, \quad (8)$$

representing the concentrations of the three chromophores. In Eq. (8), E is the matrix of molar extinction coefficients having elements $\epsilon(i, \lambda)$, for the i'th chromophore at different wavelengths.

The spectral character of the reduced scattering coefficient also provides information about the composition of the tissue. From an approximation to Mie scattering theory, it is possible to derive a relation between $\mu'_s$ and wavelength given by:

$$\mu'_s(\lambda) = A\lambda^{-b}, \quad (9)$$

where b is the scattering power and A is the scattering amplitude (which depend on scatterer size and number density). Typically, large scatterers have lower b and A values. These scattering parameters appear to reflect variations in structural breast composition associated with age and radiographic density.

In one embodiment, MR data may provide absolute blood volume, water and/or lipid concentrations. When the absolute blood volume, water and lipid concentrations are input into Eq. (7), unknown values are reduced so that the reconstruction may solve only for oxy or deoxy hemoglobin, scatter and exogenous contrast. Such a decrease in the number of unknowns provides a potentially more accurate quantification, and may reduce the time needed to perform the reconstruction.

Phantom Studies

A two-layer gelatin phantom with a cylindrical inclusion embedded inside the inner layer was used to evaluate the ability of the NIR-MR algorithm. Each gel layer possessed a different absorption and reduced scattering coefficient. When the MR data was neglected, and amplitude and phase data were reconstructed with a standard Newton type reconstruction, the root mean square (rms) error of the recovered distributions of the absorption and reduced scattering coefficients were estimated to be 0.0023 and 0.230, respectively. When the full MR data set was utilized, and MR-derived priors guided the reconstruction, the rms error of the absorption and reduced scattering coefficient images decreased 43% to 0.0014, and 55% to 0.104, respectively. The mean value of the absorption coefficient estimated in the region of the inclusion was accurate to within 10%, and estimation of the reduced scattering coefficient improved to within 20%.

A second phantom, having a homogeneous body with a 22 mm cylindrical cavity filled with a 3:1 absorption contrast intralipid solution, was also studied. When prior information was used in image reconstruction, the rms error of the absorption and reduced scattering coefficient images decreased from 0.0019 to 0.0014 (26%) and from 0.1444 to 0.0613 (58%), respectively.

Figure 12:
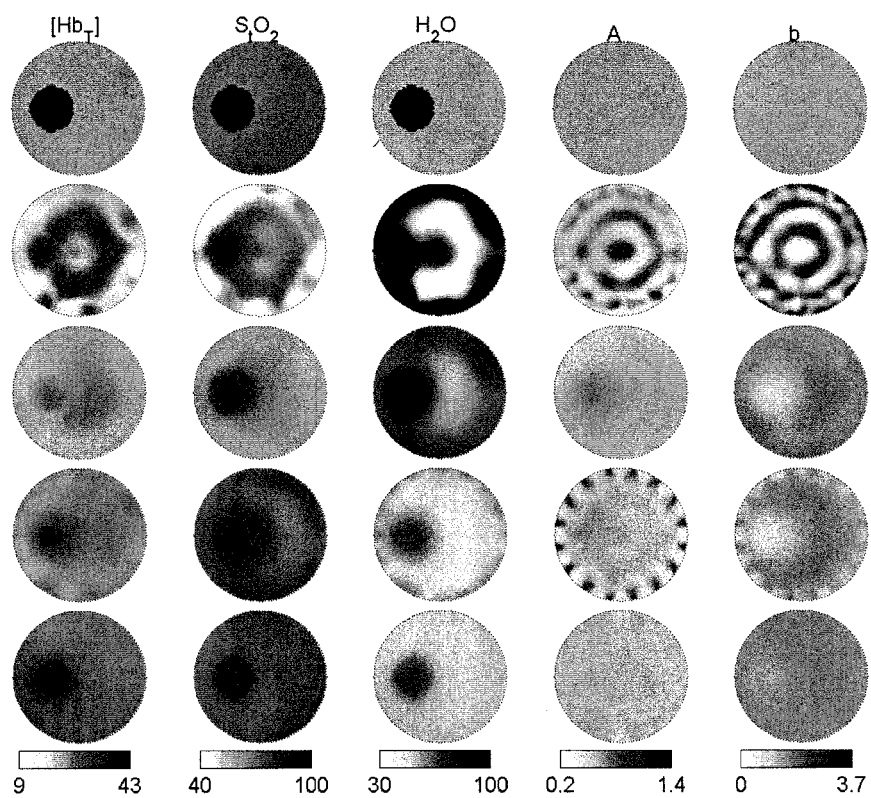
FIG. 12 illustrates chromophore and scatter parameters for a tissue phantom using various model constraints, according to multiple embodiments.

FIG. 12 illustrates chromophore and scatter parameters for a tissue phantom using various model constraints. The top row shows true properties of the phantom including: total hemoglobin concentration ($\mu$M), [Hb$_T$]; oxygen saturation (%), S$_t$O$_2$; water (%), H$_2$O; scattering amplitude, A; and scattering power, b. The second row from the top illustrates a NIR reconstruction using no priors. It can be seen that the conventional method (no priors) yields images with considerable artifacts. The middle row illustrates a reconstruction incorporating spatial priors from MR data. Spatial priors remove the artifacts, so that the inclusion is clearly visible and matches the expected size and shape. However, the [Hb$_T$] contrast is significantly underestimated; the recovered mean in the region of the anomaly reaches only 57% of the true value. The second row from the bottom illustrates a reconstruction incorporating spectral priors from MR data. The spectral priors show substantial improvement in the quantification with the mean [Hb$_T$] at 78% of the true value. The bottom row incorporates both spatial and spectral priors. The application of both constraints results in images with a further reduction in artifacts close to the boundary, and the mean [Hb$_T$] reaches 88% of the expected value.

The changes described above, and others, may be made in the devices and methods described herein without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and device, which, as a matter of language, might be said to fall there between.

What is claimed is:

1. A system for combined optical imaging and magnetic resonance imaging of breast tissue, comprising:
    a Magnetic Resonance Imaging (MRI) system;
    a plurality of protrusions, formed on a housing, the housing adapted to be releaseably secured to a grid such that each protrusion projects through a hole of the grid;
    each protrusion including an optical window covered by a material transparent to a preselected range of electromagnetic energy;
    the grid being a grid of a Magnetic Resonance Imaging (MRI) breast tissue compression system, wherein each protrusion is configured to releasably mates with a grid hole of the grid;
    a plurality of light sources coupled to at least some windows of the protrusions;
    a plurality of light detectors coupled to receive light from at least some windows of the protrusions;
    and a computer;
    wherein the computer is configured with firmware comprising machine readable instructions that, when executed, reconstructs a near-infrared (NIR) tomographic image of breast tissue from light received by the light detectors;
    wherein the firmware that reconstructs the NIR image is constrained by MRI breast image data acquired by the MRI imaging system; and
    wherein the magnetic resonance breast image data provides quantification data of one or more of lipid concentration, and water concentration, wherein the quantification data is used in reconstructing the NIR image, and wherein the NIR image further comprises quantification of deoxyhemoglobin.

2. The system of claim 1 where the MR and NIR data are acquired simultaneously.

* * * * *